United States Patent [19]

Meyer et al.

[11] Patent Number: 5,750,092
[45] Date of Patent: May 12, 1998

[54] SUNLESS TANNING COMPOSITION AND METHOD

[75] Inventors: Thomas A. Meyer, Germantown; Michael E. Ando; Jimmy B. Powell, both of Memphis, all of Tenn.

[73] Assignee: Schering-Plough HealthCare Products, Inc., Memphis, Tenn.

[21] Appl. No.: 820,324

[22] Filed: Mar. 12, 1997

Related U.S. Application Data

[60] Provisional application No. 60/013,547, Mar. 14, 1996.
[51] Int. Cl.$^6$ .............................. A61K 7/42; A61K 7/44; A61K 7/00
[52] U.S. Cl. .............................. 424/59; 424/60; 424/400; 424/401
[58] Field of Search .............................. 424/59, 60, 400, 424/401

[56] References Cited

U.S. PATENT DOCUMENTS

| | | | |
|---|---|---|---|
| 3,177,120 | 4/1965 | Black et al. | 167/90 |
| 4,458,811 | 7/1984 | Wilkinson | 206/219 |
| 4,466,805 | 8/1984 | Welters et al. | 8/406 |
| 4,496,046 | 1/1985 | Stone et al. | 206/219 |
| 4,608,043 | 8/1986 | Larkin | 604/87 |
| 4,609,544 | 9/1986 | Herlihy | 424/59 |
| 4,772,471 | 9/1988 | Vanlerberghe et al. | 424/450 |
| 4,968,497 | 11/1990 | Wolfram et al. | 424/59 |

FOREIGN PATENT DOCUMENTS

| | | |
|---|---|---|
| 0 424 282 A1 | 4/1991 | European Pat. Off. . |
| 0 547 864 A1 | 6/1993 | European Pat. Off. . |
| WO 94/13258 | 6/1994 | WIPO . |
| WO 94/22419 | 10/1994 | WIPO . |
| WO 95/15742 | 6/1995 | WIPO . |
| WO 95/26179 | 10/1995 | WIPO . |

OTHER PUBLICATIONS

E. Wittgenstein et al., "Reaction of Dihydroxyacetone (DHA) with Human Skin Callus and Amino Compound," *Journal of Investigative Dermatology*, vol. 36, pp. 283–286, 1991.

A. Meybeck, "A Spectroscopic Study of the Reaction Products of Dihydroxyacetone with Aminoacids," *Journal of the Society of Cosmetic Chemists*, vol. 28, pp. 25–35, 1977.

*Chemical Abstracts*, vol. 95, abstracts 30226g, 1981.

M. F. Bobin et al., "Effects of Color Adjuvants on the Tanning Effect of Dihydroxyacetone," *Journal of the Society of Cosmetic Chemists*, vol. 35, pp. 265–272, 1984.

*Primary Examiner*—Shelley A. Dodson
*Attorney, Agent, or Firm*—Robert A. Franks

[57] ABSTRACT

A simulated skin tan is obtained by simultaneously or sequentially applying a fluid formulation comprising dihydroxyacetone and a fluid formulation comprising a secondary polyamine, wherein the polyamine formulation also contains a color modifier which is: an amino acid; a substituted ethylenediamine; and mixtures of any two or more of the foregoing.

41 Claims, No Drawings

SUNLESS TANNING COMPOSITION AND METHOD

This application claims benefit to provisional applicant No. 60/013,547 filed Mar. 14, 1996.

FIELD OF THE INVENTION

This invention relates to a composition and method which are useful in the simulated tanning of skin. More particularly, the invention relates to the treatment of skin with dihydroxyacetone compositions, to form a brownish coloration thereon.

INTRODUCTION TO THE INVENTION

It has long been known that certain compounds form pigments when applied to the skin. Products containing dihydroxyacetone (frequently simply abbreviated "DHA") have been marketed since the early 1960's, and have been found satisfactory by many persons who wish to give their skin the appearance of an attractive tan, but do not desire to risk the now well-appreciated health hazards of exposure to solar or artificially-generated ultraviolet radiation.

However, some persons have not obtained the desired results from DHA applications. A small number of individuals develop a coloration which tends to appear yellowish or orange. Some others, probably due to perspiration, rubbing or washing during the slow generation of color as skin components react with DHA, or to a lack of care to evenly apply the DHA, develop uneven coloration.

The chemistry of DHA-skin interaction has been investigated by several workers. Wittgenstein and Berry published a paper "Reaction of Dihydroxyacetone (DHA) with Human Skin Callus and Amino Compounds," in *The Journal of Investigative Dermatology*, Vol. 36, pages 283–286 (1961), describing work to characterize the browning phenomenon. They reported that DHA reacts with a number of compounds, including ammonia and amino acids, to form a brown color, and theorized that skin browning is due to the reaction of DHA with free amino groups in the skin, the amino groups probably being on arginine molecules which are present in skin proteins.

A. Meybeck published "A Spectroscopic Study of the Reaction Products of Dihydroxyacetone with Aminoacids" in *Journal of the Society of Cosmetic Chemists*, Vol. 28, pages 25–35 (1977), and characterized brown pigments formed from the reaction of DHA with amino and other acids at 100° C. Further experiments at 37° C. were conducted to better simulate reactions which may occur in the skin: DHA was reacted with the amino acids glycine, lysine, alanine, serine and arginine, but only glycine and lysine produced significant amounts of pigment after 24 hours. It was concluded that DHA must act by initially condensing with free amino acids at the skin surface, followed by polymerization and linking to proteins in the stratum corneum, probably through lysine side chains.

A further study was reported by M. F. Bobin, M. C. Martini and J. Cotte, "Effects of Color Adjuvants on the Tanning Effect of Dihydroxyacetone," *Journal of the Society of Cosmetic Chemists*, Vol. 35, pages 265–272 (1984). This work involved measuring the rate of color development after mixing DRA and various amino acids or their derivatives, and applications of DHA and methionine sulfoxide in vivo. It was concluded that methionine sulfoxide is a useful adjuvant to DHA, as the combination provided rapid color development, plus a more intense and long lasting color than would be obtained with only DHA. This result was thought to result from the affinity of methionine sulfoxide for keratin.

*Chemical Abstracts*, Vol. 95, abstract 30226g (1981) summarizes a German patent document (3,037,497) pertaining to dyeing skin, hair, feathers, fur, etc. by treating with a mixture of DHA and an amino acid sulfoxide. When DHA and methionine sulfoxide were applied in cream formulations, skin turned a deep brown color after three hours and the color was more resistant to washing than that obtained with only DHA.

Black et al., in U.S. Pat. No. 3,177,120, discussed the problem of including DHA and amino group-containing sunscreens together in a formulation, and concluded that only sunscreens free from amino groups should be used, to prevent formation of a yellow or brown color in the storage container; color formation is also said to be accompanied by inactivation of both the DHA and sunscreen.

Two of the present inventors, in a PCT International Patent Application published on Jun. 23, 1994 as WO 94/13258, described the improvement in color development rate which can be obtained by providing a two-formulation sunless tanning apparatus and method, wherein one formulation comprises dihydroxyacetone and the other comprises a secondary polyamine.

It is now desired to provide formulations and a method for browning skin to form simulated tans having further improved color development rates and colors which more closely resemble those obtained from exposure of the skin to ultraviolet radiation.

SUMMARY OF THE INVENTION

The invention, in one aspect, includes a method for imparting artificial tan to skin, comprising simultaneously or sequentially contacting the skin with dihydroxyacetone, a secondary polyamine and a color modifier which is selected from an amino acid, a substituted ethylenediamine, a carboxylic acid or a mixture of any two or more of the foregoing. Also included is a composition for immediate application to skin, comprising dihydroxyacetone, at least one secondary polyamine and a color modifier. Further included is a kit for sunless tanning comprising a formulation containing dihydroxyacetone and a formulation containing a secondary polyamine and a color modifier.

DETAILED DESCRIPTION OF THE INVENTION

In the description and claims, all composition percentages are expressed on a weight basis, unless otherwise noted.

To use the invention, there will preferably be provided apparatus having separate compartments for a formulation containing dihydroxyacetone and a formulation containing the secondary polyamine. As previously noted in the art, it is desirable to prevent mixing of the components until a user is ready to make a skin application, to prevent premature reaction and color formation. The apparatus should preferably be configured to simultaneously dispense the formulations, in desired amounts, or to sequentially dispense them. If sequentially dispensed, the formulations can be mixed before spreading onto the skin, or can be spread in the order of dispensing.

Both formulations must be fluid, that is, capable of flow under the influence of gravity or a moderate externally applied pressure. Examples of useful fluid formulations are ointments, dispersions such as creams and lotions, gels, solutions, and the like, each of which (and preparative techniques therefor) are very well known to those skilled in the formulating art.

Typically, both formulations which are to be used together will be of the same type, e.g., if one is a gel, the other also will be a gel to facilitate application and mixing. However, it is not always necessary to observe this general principle.

Polyamines which are useful in preparing the formulations of the invention have the general formula $R^1NH(CH_2)_2NHR^2$, where $R^1$ and $R^2$ are independently hydrogen, alkyl, cycloalkyl, aromatic or silicon-containing groups having up to about 22 carbon atoms, provided that both of $R^1$ and $R^2$ cannot be hydrogen.

The above polyamines which are useful in preparing the formulations of the invention include silanols and alkoxysilanes having the general formula:

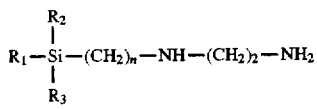

where $R_1$ and $R_2$ are hydroxy and $R_3$ is hydrogen, hydroxy or an alkyl, cycloalkyl or aryl group having up to about 22 carbon atoms; or $R_1$ and $R_2$ are the same or different alkoxy groups having up to about 22 carbon atoms and $R_3$ is a hydroxy, alkoxy, cycloalkoxy or aryloxy group having up to about 22 carbon atoms; and n is an integer of 2 or 3.

The terms "alkyl," "alkoxy," "cycloalkyl," "cycloalkoxy," "aryl" and "aryloxy" are used herein to refer to both substituted and unsubstituted groups, the alkyl and alkoxy groups being branched or unbranched, permissible substituents for any group including hydrocarbon groups, halogen or halogen-containing groups, nitrogen-containing groups, sulfur-containing groups, hydroxy or hydroxy-containing groups, carbonyl or carbonyl-containing groups, silicon-containing groups and the like. In many instances, the groups will be purely hydrocarbon groups.

Secondary polyamines for use in the present invention include N-substituted ethylenepolyamines. In general, it has been found that N-substituted ethylenepolyamines generate browning end products with dihydroxyacetone somewhat more quickly, and in higher yields, than either of N,N'-disubstituted ethylenepolyamines or primary amines. In general, the substituent for an N-substituted ethylenepolyamine will preferably have about 6 to about 22 carbon atoms.

Preferred substituted ethylenediamines for use in the invention are silanols and alkoxysilanes, such as N-[3-(trihydroxysilyl)-propyl]-ethylenediamine which is commercially available in a 25 percent aqueous solution as HYDROSIL™ 2776 from Huls America of Piscataway, N.J., U.S.A.

A color modifier is also present at the time of mixing or applying the DHA and polyamine formulations. For convenience, this color modifier is typically a component of the polyamine formulation, as it is a type of compound which may react prematurely with DHA to form a color if included in that formulation. The color modifier is used in amount ranges similar to those of the polyamine, generally about 0.01 to about 15 percent by weight of their formulations. The molar ratios of polyamine to color modifier range from about 0.01 to about 50.

Useful color modifying compounds include: amino acids; substituted ethylenediamines having the formula $L-(CH_2)_n-NH-(CH_2)_2-NHM$, wherein L is OH or COOH, M is hydrogen or $L-(CH_2)_n$, and each n independently is an integer of 1 to about 22; carboxylic acids having either of the formulae $HOOC-(CH_2)_n-COOH$ or $R-CH(OH)-COOH$, wherein n is an integer up to about 22 and R is hydrogen or an alkyl, cycloalkyl or aryl group having up to about 22 carbon atoms; and mixtures of any two or more of the foregoing.

Volumes and active ingredient concentrations of dispensed formulations should be chosen to provide molar ratios of DHA to polyamine about 0.2 to about 200. More preferably, the ratios should be about 1 to about 100. Still more preferred are molar ratios about 5 to about 66. If the number of moles of DHA exceed the number of moles of polyamine, a portion of the DHA will remain free to react with amino groups in the skin, increasing the substantivity of the color-formed; thus, a molar excess of DHA is preferred. Although the rate of color formation in the skin (with free amino groups present there) is considerably slower than that of DHA with provided secondary polyamine on or near the skin surface, color formed in the skin is more resistant to removal by washing and abrasion. For this reason, it is preferable to establish both the early and frequently more intense color on the skin surface, and the more permanent but slower forming color in the skin layers.

It has been found that pH at the time of application affects the resulting color. In general, either the DHA formulation or the polyamine formulation should be able to establish pH values about 3 to about 13 locally when applied to the skin. More preferred are values about 5 to about 9, with values about 6 to about 7 being particularly preferred with most formulations. The optimal pH for a given polyamine application will be somewhat dependent upon the pKa of that polyamine, and can be easily determined by applying formulations having different pH values to the skin.

To compare simulated tans created by different means, it is helpful to have an objective, instrumental measurement of colors and intensities. Accordingly, a method has been developed using the Minolta Chroma Meter CR-200, which uses reflected light from a surface and gives results in terms of the CIE (International Commission on Illumination) tristimulus values. These values are subsequently transformed mathematically into the L* a* b* color space, wherein the magnitudes of changes in hue and intensity of color correspond closely with those perceived by the human eye.

L*, being achromatic, ranges from black (L*=0) to white (L*=100); this term is called "metric lightness" and is a measure of how light or dark a color is, relative to a matching shade of gray. Hue is measured in terms of the chromaticity coordinates a* and b*, where a* indicates redness (a*>0) and b* indicates yellowness (b*>0). The values of a* and b* can be plotted with a* as the x-axis and b* as the y axis, to give quantitative color information: "metric chroma" is the length of a line from the origin (a*=0, b*=0) to the point of a sample reading, while "metric hue angle" is the angle between the a* axis and the metric chroma line. Metric chroma indicates the strength of a color response (i.e., the extent to which a color differs from its matching shade of gray). Metric hue angle quantifies hue in degrees, with larger values indicating more yellow hues and smaller values indicating more red (or less yellow) hues.

The meter is used to measure natural tans with a number of subjects, to establish a target for the appearance of tans produced by DHA reactions. In general, it is found that points on a chromaticity plot for dark tans will have b* from about 19 to about 24, with a* ranging from about 10 to about 14. For medium tans, b* will be about 20 to about 24, with a* from about 9 to about 12. For light tans, b* will be about 18 to about 20, with a* about 7 to about 10. Rather than being a point, the target color is represented by the area on the plot where natural tans lie. Values of metric chroma increase steadily as tans progress from light to medium, but increase much more slowly as tans become more dark than "medium." In contrast, values of metric hue angle overlap significantly for light, medium and dark tans, except for very dark tans which have increased redness (decreased metric hue angle).

Metric lightness is the third required parameter for characterizing natural tans. L* values decrease as tans become darker, a difference of about one unit being discernable to a trained observer. For natural tans, L* ranges from about 47 to about 53 for dark tans, about 54 to about 57 for medium tans and about 58 to about 64 for light tans.

The meter is also used to measure the characteristics of simulated tans obtained using only DHA applications. Several subjects are treated with an oil in water emulsion containing 5 percent DHA, with applications (2 mg DHA/ $cm^2$) being made once each day for four days. After the first day, values for b* are about 13 to about 21, the a* values are about 3 to about 8 and L* values are about 63 to about 74. After two days, b* is about 15 to about 23, a* is about 5 to about 8 and L* is about 62 to about 72. After the third day, b* is about 16 to about 23, a* is about 5 to about 9 and L* is about 61 to about 71. After four days, b* is about 17 to about 24, a* is about 5 to about 9 and L* is about 61 to about 70. The hues for all but a few of the readings are more yellowish than the tan target area, and all but a few of the readings indicate tans more light than natural tans, even though comparable levels of metric chroma are generated. It can generally be stated that simulated tans using only DHA are more yellow and lighter than natural tans having similar extents of color formation.

The following examples are provided to illustrate various aspects of the invention, and are not to be construed as limiting the invention in any manner. Abbreviations for chemical composition names are used without definition, following their first occurrence.

EXAMPLE 1

To compare hue development changes caused by addition of organic acids to dihydroxyacetone-amine mixtures, an in vitro model is used. In this model, Whatman Grade 3MM chromatography paper is cut into strips 2 cm wide and 18 cm long. Equal volumes of DHA solutions and trihydroxysilyl-propylethylenediamine ("TSPEI") solutions, either with or without a color modifying organic acid, are mixed and a 0.20 ml volume of the mixture is immediately drawn into an automatic pipet and applied to a 5 cm length of the paper strip. Application is made by gradually moving the pipet upward from the bottom of the strip, so that the solution is uniformly absorbed into the desired area. The strips are then placed into an oven maintained at 30° C., and color is allowed to develop for about 16 hours.

After removal from the oven, the strips are measured for color with the Minolta Chroma Meter CR-200. Hues are dissected into metric chroma (dC*, the extent of color formation) and metric lightness (dL*, the darkness of color) changes by subtracting the paper's white color from the colors formed after reaction.

In the table below, data are obtained by mixing equal volumes of: (1) an aqueous 30 percent ethanol solution containing 1 percent TSPE, to which a sufficient quantity of the identified acid is added to adjust pH to 7; and (2) an aqueous 30 percent alcohol solution containing 4 percent DHA. Commercially available forms of α-hydroxy acids are obtainable from Barnet Products Corp. of Englewood Cliffs, N.J., U.S.A. and are identified by the abbreviations "MFA" (MFA™ Complex solution containing 30–40 percent total acid and 0.6 percent of the preservative phenoxyethanol) and "Biolac" (BIOLAC™ Natural Lactic Acid solution containing 28–35 percent lactic acid and preservatives: 0.6 percent phenoxyethanol and 0.2 percent methylparaben).

| Acid Type | dL* | dC* | IdC*I-IdL*I |
|---|---|---|---|
| HCl | −15.8 | 26.8 | 11.0 |
| Malonic | −21.7 | 31.3 | 9.6 |
| Adipic | −18.8 | 29.6 | 10.8 |
| Pimelic | −16.3 | 28.5 | 12.2 |
| Lactic | −17.0 | 27.4 | 10.4 |
| MFA | −18.8 | 29.2 | 10.4 |
| Biolac | −20.4 | 29.2 | 8.8 |

As color forms on the strips, C* values increase and L* values decrease. Therefore, after the initial white color is subtracted, dC* values are positive and dL* values are negative. In the foregoing table, a more negative dL* indicates darker color, and a more positive dC* indicates greater extent of color formation. The |dC*|-|dL*| value provides a measure of a color's chroma (i.e., strength) relative to its darkness. For comparable chroma levels, lower values indicate darker colors.

This has particular relevance for sunless tanning, since the commercially available products yield skin colors which are too light for the level of chroma formed. The |dC*|-|dL*| values quantitate this color imbalance and provide a means for determining whether changes in C* and L* lead to bonafide improvements. For example, increases in C* with comparable decreases in L* do not represent improvements in color quality, even though more color is present. It is desired to produce a greater change in L* than is obtained in C*.

As compared to hydrochloric acid, the organic acids produce small but discernable increases in the extent and darkness of colors formed. The absolute differences between dC* and dL* indicate that (except in the case of pimelic acid) the organic acids yield darker colors.

EXAMPLE 2

The test of the preceding example is conducted with the same DHA solutions and comparable TSPE solutions containing, in place of the acids, the amines listed in the table below. In each case, the TSPE solution is adjusted to pH 7 with hydrochloric acid.

Abbreviations in the table are as follows: "HEED" is N,N'-bis(2-hydroxyethyl)ethylenediamine; "EDDA" is ethylenediamine-N,N'-diacetic acid; and "HPED" is N-(3-hydroxypropyl)ethylenediamine.

| Percent Amine | dL* | dC* | IdC*I-IdL*I |
|---|---|---|---|
| None | −15.8 | 26.8 | 11.0 |
| GLYCINE | | | |
| 0.5 | −19.9 | 29.4 | 9.5 |
| 1.0 | −22.3 | 30.0 | 7.7 |
| 1.5 | −24.3 | 29.3 | 5.0 |
| 2.0 | −25.4 | 28.9 | 3.5 |
| 3.0 | −27.4 | 26.9 | −0.5 |
| SERINE | | | |
| 1.0 | −18.7 | 28.6 | 9.9 |
| 2.0 | −20.1 | 28.3 | 8.2 |
| 4.0 | −22.3 | 28.5 | 6.2 |

-continued

| Percent Amine | dL* | dC* | \|dC*\|-\|dL*\| |
|---|---|---|---|
| THREONINE | | | |
| 1.0 | −21.6 | 28.5 | 6.9 |
| 2.0 | −24.0 | 29.3 | 5.3 |
| 4.0 | −25.0 | 29.7 | 4.7 |
| 6-AMINOCAPROIC ACID | | | |
| 0.5 | −22.3 | 29.6 | 7.3 |
| 1.0 | −22.3 | 29.6 | 7.3 |
| 1.5 | −24.7 | 27.7 | 3.0 |
| 2.0 | −26.7 | 27.6 | 0.9 |
| 3.0 | −30.0 | 26.7 | −3.3 |
| HEED | | | |
| 0.2 | −19.9 | 25.1 | 5.2 |
| 0.4 | −21.2 | 24.4 | 3.2 |
| 0.6 | −23.3 | 25.0 | 1.7 |
| 0.8 | −23.7 | 25.7 | 2.0 |
| EDDA | | | |
| 1.0 | −22.0 | 29.5 | 7.5 |
| HPED | | | |
| 1.0 | −20.2 | 27.6 | 7.4 |

As shown above, the addition of an amine modifier increases both extent and darkness of the formed color. However, the major effect is a substantial increase in color darkness.

Of the amino acids tested, the largest effect is obtained with glycine and 6-aminocaproic acid. The largest effect of any amine compound additive tested is obtained with HEED. Particularly at the higher additive concentrations, all compounds yield large visually discernable hue differences, over the color formed without any additive.

EXAMPLE 3

The test of the preceding examples is conducted using the same DHA solutions and comparable TSPE solutions containing both acid and amine additives. Results are as in the following table, where compound abbreviations are as in the preceding examples and the customary abbreviations are used for the amino acids glycine, arginine, serine, threonine, lysine and glutamic acid.

| Percent Amine | Acid | dL* | dC* | \|dL*\|-\|dC*\| |
|---|---|---|---|---|
| None | HCl | −15.8 | 26.8 | 11.0 |
|  | MA | −21.4 | 31.3 | 10.0 |
| 2.0 Gly | HCl | −20.6 | 27.7 | 7.1 |
|  | MA | −24.6 | 29.6 | 5.0 |
| 4.7 Arg | HCl | −19.3 | 26.7 | 7.4 |
|  | MA | −22.6 | 28.7 | 6.1 |
| 2.8 Ser | HCl | −20.5 | 28.2 | 7.7 |
|  | MA | −22.8 | 29.7 | 6.9 |
| 3.2 Thr | HCl | −23.2 | 27.9 | 4.7 |
|  | MA | −24.6 | 30.0 | 5.4 |
| 4.9 Lys | HCl | −20.3 | 27.4 | 7.1 |
|  | MA | −22.6 | 28.1 | 5.5 |
| 3.9 Glu | HCl | −19.3 | 28.0 | 8.7 |
|  | MA | −24.2 | 31.1 | 6.9 |
| 0.2 HEED | HCl | −19.9 | 25.1 | 5.2 |
|  | MA | −28.9 | 28.4 | −0.5 |
| 0.4 HEED | HCl | −21.2 | 24.4 | 3.2 |
|  | MA | −26.5 | 25.6 | −0.9 |
| 0.6 HEED | HCl | −23.3 | 25.0 | 1.7 |
|  | MA | −29.0 | 28.7 | −0.3 |
| 0.8 HEED | HCl | −23.7 | 25.7 | 2.0 |
|  | MA | −30.8 | 28.9 | −1.9 |
| 1.0 EDDA | HCl | −22.0 | 29.5 | 7.5 |
|  | MA | −26.2 | 30.5 | 4.3 |

As shown by these results, the combination of malonic acid and amino additive produces more desirable colors, than those obtained with hydrochloric acid.

EXAMPLE 4

The test of the preceding examples is conducted using the same DHA solutions and comparable TSPE solutions containing amine (2.0 percent HEED) additive and sufficient amounts of an acid to adjust pH to 7. Results are as in the following table, where compound abbreviations are as in the preceding examples.

| Acid | dL* | dC* | \|dC*\|-\|dL*\| |
|---|---|---|---|
| HCl | −17.6 | 26.9 | 9.4 |
| MFA | −23.2 | 26.4 | 3.2 |
| Biolac | −25.4 | 26.4 | 1.1 |
| Lactic | −27.5 | 27.2 | −0.3 |
| Malonic | −29.4 | 30.0 | 0.3 |

These results indicate the effectiveness of α-hydroxy acids and dicarboxylic acids in obtaining desirable color modifications.

EXAMPLE 5

A gel base is prepared, using the following components:

| | |
|---|---|
| 600 grams | SD Alcohol 40 |
| 1070 grams | Water |
| 30 grams | Polyquaternium 10 (UCARE ™ Polymer JR-30M, Amerchol Corporation, Edison, New Jersey, U.S.A.) |

The gel is prepared by dissolving the polymer in the water with stirring over a period of about 1 hour, to form a thick solution, then slowly adding the alcohol and continuing stirring until a uniform clear gel is obtained.

The base gel is used to prepare 4 percent DHA gel, by combining an 85 gram portion with a mixture of 11 grams water and 4 grams DHA, and stirring until uniform. This is component "A" in the following table.

The base gel is used to prepare 1 percent TSPE gel by combining 85 grams of gel, 4 grams TSPE, 10 grams water and 1 gram HCl (to adjust pH to 7). This is component "B" in the following table.

A 4 percent DHA solution is prepared by dissolving 4 grams DHA in 96 grams of a 30 percent aqueous solution of ethanol. This is component "C" in the following table.

A 1 percent TSPE solution containing glycine is prepared by combining 62 grams water with 30 grams ethanol, 4 grams TSPE, 2 grams glycine and 2 grams HCl to adjust pH to 7, then stirring until a uniform solution is obtained. This is component "D" in the following table.

A 1 percent TSPE solution containing HEED and MFA is prepared by combining 91.5 grams of a 30 weight percent aqueous ethanol solution, 4 grams TSPE, 0.5 grams HEED and 4 grams MFA to adjust pH to 7, then stirring until a uniform solution is obtained. This is component "E" in the following table.

An experiment is performed with human volunteers to determine differences in skin coloration obtained when DHA and the above TSPE solutions are applied. Sites measuring 5 cm×5 cm are outlined using a template and an indelible marker. Initial color measurements are made of the sites with a Minolta Chroma Meter CR-200. Inside each site are placed 25 μl of a DHA formulation and 25 μl of a TSPE formulation. The formulations are then rubbed into the skin, taking care to not spread any material outside of the site boundaries. After 4 hours, color measurements are again taken with the meter.

The following table shows average differences between meter readings before treatment and meter readings after treatment, obtained from measurements on the indicated number of subjects for each formulation type.

| Components | Subjects | dL* | dC* | IdC*I-IdL*I |
|---|---|---|---|---|
| A, B | 15 | -4.21 | 5.56 | 1.35 |
| C, D | 20 | -4.91 | 5.20 | 0.29 |
| C, E | 21 | -5.28 | 5.10 | -0.18 |

In vitro studies with the filter paper strips predict that the three formulations should generate similar extents of color, as indicated by dC* values, but that glycine and HEED-MFA additives should cause the generated colors to be darker. This prediction is correct, as shown by the above data.

EXAMPLE 6

Substantivity indicates, at least partly, the water solubility of the color formed. A suitable test involves measuring skin color with the Minolta Chroma Meter, applying formulations to the skin, allowing color to develop for four hours, then repeating the color measurement. A final skin color measurement is taken 24 hours later, after the subjects have bathed according to their daily routine. Values of ΔE, which represents total color difference between treated and untreated skin, can be calculated from the following equation:

$$[(L^*_U-L^*_T)^2+(a^*_U-a^*_T)^2+(b^*_U-b^*_T)^2]^{1/2}$$

where the subscripts "U" represent readings with untreated skin and the subscripts "T" represent readings with treated skin.

The following results are obtained with various color modifiers applied with TSPE plus DHA, as compared with DHA applications only. For each test, a 25 cm² area of inner forearm skin is used and 25 μl each of DHA formulation (4 percent DHA) and TSPE formulation (1 percent TSPE, except "*" indicates 0.5 percent TSPE and "**" indicates 0.3 percent TSPE) containing the indicated amount of modifier are applied. The "HCl" or "MFA" entry in the table identifies the acid used to adjust pH of the TSPE-modifier formulation to 7.0.

In the results, "% Color Remaining" is calculated by the equation ($\Delta E_{24\ HOURS}/\Delta E_{4\ HOURS} \times 100$), while "Color Increase" is calculated by ($\Delta E_{DHA+TSPE}/\Delta E_{DHA\ ALONE}$). The value of $\Delta E_{DH\ ALONE}$ used for these calculations is a mean obtained from several different studies, involving different formulation types having differing DHA concentrations but a constant applied amount of DHA. Abbreviations are used, as in preceding examples.

| Modifier | Percent | Color Remaining | Color Increase |
|---|---|---|---|
| None, HCl | — | 78 | 2.2 |
| Gly, HCl | 1.0 | 71 | 2.0 |
| | 1.5 | 63 | 1.9 |
| | 2.0 | 61 | 1.8 |
| Ser, HCl | 1.0 | 76 | 1.8 |
| | 2.0 | 71 | 2.0 |
| | 3.0 | 69 | 1.7 |
| Thr, HCl | 0.8 | 75 | 2.2 |
| | 1.6 | 73 | 2.1 |
| | 3.2 | 71 | 2.0 |
| HEED, MFA | 0.25 | 70 | 2.2 |
| | 0.5 | 67 | 2.2 |
| | 1.0 | 64 | 2.1 |
| EDDA, HCl | 0.5 | 73 | 2.7 |
| | 1.0 | 69 | 2.5 |
| | 2.0 | 64 | 2.4 |
| HEED, MFA* | 0.5 | 80 | 1.8 |
| HEED, MFA** | 0.25 | 75 | 1.4 |

These results demonstrate that the color modifiers do not adversely affect substantivity of the color formed by DHA and TSPE applications to skin.

EXAMPLE 7

Lotions containing dihydroxyacetone are prepared using the following ingredients, where the "6%" "8%" and "10%" columns indicate the final DHA concentration obtained. The amounts of the components are expressed in grams, for obtaining 100 grams of lotion. In each case, there is an initial excess of water, to compensate for evaporation which occurs during the preparation.

| Component | 6% | 8% | 10% |
|---|---|---|---|
| Part A | | | |
| USP purified water | 74.45 | 72.45 | 70.45 |
| Sodium chloride | 0.50 | 0.50 | 0.50 |
| Dihydroxyacetone | 6.00 | 8.00 | 10.00 |
| Part B | | | |
| Preservative | 1.00 | 1.00 | 1.00 |
| Part C | | | |
| Emulsifier * | 3.00 | 3.00 | 3.00 |
| Cetyl dimethicone | 1.00 | 1.00 | 1.00 |
| Cyclomethicone | 6.00 | 6.00 | 6.00 |
| Isopropyl palmitate | 3.70 | 3.70 | 3.70 |
| Light mineral oil | 3.70 | 3.70 | 3.70 |
| Jojoba oil | 0.10 | 0.10 | 0.10 |
| Aloe vera lipoquinone | 0.10 | 0.10 | 0.10 |
| Vitamin E acetate | 0.10 | 0.10 | 0.10 |
| Dimethicone | 0.10 | 0.10 | 0.10 |
| Part D | | | |
| Fragrance | 0.25 | 0.25 | 0.25 |

* The emulsifier is a mixture of polyglyceryl-4 isostearate, cetyl dimethicone copolyol and hexyl laurate, and is available from Goldschmidt Chemical Corporation, Hopewell, Virginia U.S.A. as Abil WE 09 ™.

The lotion is prepared by adding each of the other Part A ingredients to the water, in their listed order, and heating to about 70° C. with mixing. After adding the preservative of Part B, the mixture is cooled to about 50° C. and mixing is continued.

In a separate container, the ingredients of Part C are combined and heated to about 50° C., with mixing.

The heated aqueous phase is added to the heated oil phase, with slow mixing. The rate of addition is sufficiently slow that visually complete emulsification occurs immediately.

After all of the aqueous phase has been added, the mixer speed is increased to ensure a stable emulsion.

After cooling the emulsion to about 45° C., the fragrance of Part D is added and mixing is continued through cooling to about room temperature.

Any of these lotions can be used in conjunction with the lotion of the following example to provide a kit for sunless tanning. Different DHA concentrations are useful for different skin tones, the lotions of this example being suitable for producing light, medium or dark simulated tans.

EXAMPLE 8

A lotion containing an amine and a color modifier is prepared using the following ingredients, to form 100 grams.

| Component | grams |
| --- | --- |
| Part A | |
| USP purified water | 77.4 |
| Hydrosil 2776 | 2.0 |
| HEED | 0.4 |
| Lactic acid, 85% concentrate | 1.3 |
| Sodium chloride | 0.5 |
| Part B | |
| Emulsifier * | 3.0 |
| Cetyl dimethicone | 1.0 |
| Cyclomethicone | 6.0 |
| Isopropyl palmitate | 3.7 |
| Light mineral oil | 3.7 |
| Part C | |
| Preservative | 1.0 |

* Emulsifier is the same as in the preceding example.

The lotion is prepared by adding the other ingredients of Part A to the water, in their listed order, and stirring until dissolved.

In a separate container, the ingredients of Part B are combined and mixed, while heating the mixture to about 50° C.

The aqueous phase is added to the heated oil phase, with slow mixing. The rate of addition is sufficiently slow that visually complete emulsification occurs immediately. After all of the aqueous phase has been added, the mixer speed is increased to ensure a stable emulsion. The preservative of Part C is added and mixing continues until the emulsion has cooled to about room temperature.

This lotion can be used in conjunction with a lotion of the preceding example, to provide a two-component kit for sunless tanning.

EXAMPLE 9

An alcoholic solution of amines is prepared by continuously stirring 340.25 grams water and sequentially adding the following:

6.00 grams TSPE, 25% aqueous solution
1.25 grams HEED
2.50 grams Lactic acid, 85% concentrate 150.00 grams SD Alcohol 40

This solution can conveniently be used to enhance simulated tans, by spraying or wiping onto the skin, preferably followed by rubbing well into the skin, before a DHA-containing solution, gel, lotion, cream, or other formulation is applied.

The invention has been described with respect to several specific embodiments, but is not to be limited to those embodiments, the scope of the invention being defined only by the appended claims. Various improvements, alternatives and equivalents will be apparent to those skilled in the art, and are included within the claimed invention.

What is claimed is:

1. A kit for imparting an artificial tan to skin, comprising:

(a) a fluid formulation comprising dihydroxyacetone; and (b) a fluid formulation comprising a secondary polyamine;

wherein there is also present in the formulation of (b) a color modifying amount of a modifier selected from the group consisting of: an amino acid; a substituted ethylenediamine having the formula

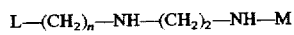

wherein L is OH or COOH, M is hydrogen or L—$(CH_2)_n$, and each n is independently an integer of 1 to about 22; a carboxylic acid having the formula HOOC—$(CH_2)_n$—COOH or R—CH(OH)—COOH, wherein n is an integer up to about 22 and R is hydrogen or an alkyl, cycloalkyl or aryl group having up to about 22 carbon atoms; and mixtures of any two or more of the foregoing.

2. The kit of claim 1, wherein at least one of dihydroxyacetone and polyamine is present in a solution.

3. The kit of claim 1, wherein at least one of dihydroxyacetone and polyamine is present in an emulsion.

4. The kit of claim 1, wherein at least one of dihydroxyacetone and polyamine is present in a gel.

5. The kit of claim 1, wherein the dihydroxyacetone is present in an emulsion and the polyamine is present in a solution.

6. The kit of claim 1, wherein a dispensing means delivers the formulations in molar ratios of dihydroxyacetone to polyamine about 0.2 to about 200.

7. The kit of claim 6, wherein there are delivered molar ratios of dihydroxyacetone to polyamine about 1 to about 100.

8. The kit of claim 6, wherein there are provided molar ratios of dihydroxyacetone to polyamine about 5 to about 66.

9. The kit of claim 1 wherein at least one formulation establishes pH values about 3 to about 13, when desired amounts of the formulations are mixed.

10. The kit of claim 9, wherein pH values about 5 to about 9 are established.

11. The kit of claim 9, wherein pH values about 6 to about 7 are established.

12. The kit of claim 1, wherein the polyamine has the formula $R^1NH(CH_2)_2NHR^2$, in which $R^1$ and $R^2$ are independently hydrogen, alkyl, cycloalkyl, aromatic or silicon-containing groups, provided that both of $R^1$ and $R^2$ cannot be hydrogen.

13. The kit of claim 1, wherein the polyamine has a hydroxysilyl group.

14. The kit of claim 1, wherein the polyamine comprises N-[3-(trihydroxysilyl)-propyl]-ethylenediamine.

15. The kit of claim 1, wherein the modifier is present in an amount about 0.05 to about 15 percent by weight of the total of the formulations.

16. The kit of claim 1, wherein the modifier comprises an amino acid.

17. The kit of claim 1, wherein the modifier comprises a substituted ethylenediamine.

18. The kit of claim 1, wherein the modifier comprises N,N'-bis(2-hydroxyethyl)ethylenediamine.

19. The kit of claim 1, wherein the modifier comprises a carboxylic acid.

20. The kit of claim 1, wherein the modifier comprises lactic acid.

21. A method for imparting artificial tan to human skin, comprising contacting the skin with a formulation containing dihydroxyacetone and a formulation containing:

(1) a secondary polyamine having the formula $R^1NH(CH_2)_2NHR^2$, wherein $R^1$ and $R^2$ are independently hydrogen, alkyl, cycloalkyl, aromatic or silicon-containing groups, provided that both of $R^1$ and $R^2$ cannot be hydrogen; and (2) a color modifier selected from the group consisting of: (a) an amino acid; (b) a substituted ethylenediamine having the formula

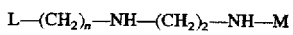

wherein L is OH or COOH, M is hydrogen or $L\text{---}(CH_2)_n$, and each n is independently an integer of 1 to about 22; (c) a carboxylic acid having the formula $HOOC\text{---}(CH_2)_n\text{---}COOH$ or $R\text{---}CH(OH)\text{---}COOH$, wherein n is an integer up to about 22 and R is hydrogen or an alkyl, cycloalkyl or aryl group having up to about 22 carbon atoms; and (d) mixtures of any two or more of the foregoing.

22. The method of claim 21, wherein the dihydroxyacetone and polyamine formulations are applied to skin sequentially.

23. The method of claim 21, wherein the dihydroxyacetone and polyamine formulations are applied to skin substantially simultaneously.

24. The method of claim 21, wherein a mixture of formulations containing dihydroxyacetone and polyamine is applied to skin.

25. The method of claim 21, wherein when the formulations are mixed the molar ratio of dihydroxyacetone to polyamine in such mixture is about 0.2 to about 200.

26. The method of claim 21, wherein when the formulations are mixed the molar ratio of dihydroxyacetone to polyamine in such mixture is about 1 to about 100.

27. The method of claim 21, wherein when the formulations are mixed the molar ratio of dihydroxyacetone to polyamine in such mixture is about 5 to about 66.

28. The method of claim 21, wherein the molar ratio of polyamine to color modifier is about 0.01 to 50.

29. The method of claim 21, wherein color modifier is present in an amount about 0.01 to about 15 percent by weight in the polyamine formulation.

30. A composition for immediate application to skin, comprising a mixture of:

(a) a formulation containing dihydroxyacetone;

(b) a formulation containing a secondary polyamine having the formula $R^1NH(CH_2)_2NHR^2$, wherein $R^1$ and $R^2$ are independently hydrogen, alkyl, cycloalkyl, aromatic or silicon-containing groups, provided that both of $R^1$ and $R^2$ cannot be hydrogen; and (c) a color modifying amount of a modifier selected from the group consisting of: an amino acid; a substituted ethylenediamine having the formula

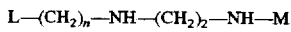

wherein L is OH or COOH, M is hydrogen or $L\text{---}(CH_2)_n$, and each n is independently an integer of 1 to about 22; a carboxylic acid having the formula $HOOC\text{---}(CH_2)_n\text{---}COOH$ or $R\text{---}CH(OH)\text{---}COOH$, wherein n is an integer up to about 22 and R is hydrogen or an alkyl, cycloalkyl or aryl group having up to about 22 carbon atoms; and mixtures of any two or more of the foregoing.

31. The composition of claim 30, wherein the polyamine has the formula $R^1NH(CH_2)_2NHR^2$.

32. The composition of claim 30, wherein $R^1$ and $R^2$ are the same.

33. The composition of claim 32, wherein $R^1$ and $R^2$ each have about 4 to about 22 carbon atoms.

34. The composition of claim 30, wherein $R^1$ and $R^2$ are different.

35. The composition of claim 31, wherein $R^1$ is hydrogen and $R^2$ has about 6 to about 22 carbon atoms.

36. The composition of claim 31, wherein $R^1$ has about 6 to about 22 carbon atoms, and $R^2$ has 1 to about 22 carbon atoms.

37. The composition of claim 30, wherein the polyamine comprises N-[3-(trihydroxysilyl)-propyl]-ethylenediamine.

38. The composition of claim 30, wherein the modifier comprises an amino acid.

39. The composition of claim 30, wherein the modifier comprises a substituted ethylenediamine.

40. The composition of claim 30, wherein the modifier comprises N,N'-bis(2-hydroxyethyl)ethylenediamine.

41. The composition of claim 30, wherein the modifier comprises a carboxylic acid.

* * * * *